United States Patent
Chester et al.

(10) Patent No.: US 7,198,711 B1
(45) Date of Patent: Apr. 3, 2007

(54) CATALYTIC CRACKING PROCESSING USING AN MCM-68 CATALYST

(75) Inventors: Arthur Chester, Cherry Hill, NJ (US); Larry Arthur Green, Mickleton, NJ (US); Sandeep Singh Dhingra, Midland, MI (US); Timothy Mason, Swedesboro, NJ (US); Hye Kyung Cho Timken, Albany, CA (US)

(73) Assignee: ExxonMobil Research and Engineering Company, Annandale, NJ (US)

( * ) Notice: Subject to any disclaimer, the term of this patent is extended or adjusted under 35 U.S.C. 154(b) by 0 days.

(21) Appl. No.: 10/468,718

(22) PCT Filed: Jan. 21, 2000
(Under 37 CFR 1.47)

(86) PCT No.: PCT/US00/01448
§ 371 (c)(1),
(2), (4) Date: Mar. 5, 2004

(87) PCT Pub. No.: WO00/43466
PCT Pub. Date: Jul. 27, 2000

(51) Int. Cl.
*C10G 47/00* (2006.01)
*C01B 39/50* (2006.01)

(52) U.S. Cl. ............ 208/108; 585/269; 585/270; 585/446

(58) Field of Classification Search .......... 585/269, 585/270, 446; 208/108
See application file for complete search history.

(56) References Cited

U.S. PATENT DOCUMENTS

| 4,740,292 A | 4/1988 | Chen et al. ............ 208/120 |
| 4,828,679 A | 5/1989 | Cormier, Jr. et al. ....... 208/120 |
| 5,472,594 A | 12/1995 | Tsang et al. ............ 208/114 |
| 6,049,018 A * | 4/2000 | Calabro et al. ............ 585/446 |

FOREIGN PATENT DOCUMENTS

| WO | WO90/04567 | 3/1990 |
| WO | WO90/04567 | 5/1990 |

OTHER PUBLICATIONS

Meier, W.M., *Atlas of Zeolite Structure Types*, 1992, pp. 8-11.

* cited by examiner

*Primary Examiner*—Glenn Caldarola
*Assistant Examiner*—Prem C. Singh
(74) *Attorney, Agent, or Firm*—Bruce M. Bordelon

(57) ABSTRACT

A process for catalytic cracking of a hydrocarbon feedstock feeds to produce an enhanced yield butylenes and isobutane comprises contacting the feedstock with a catalyst composition comprising MCM-68. The MCM-68 may be used as the primary cracking catalyst or may be used as an additive component in conjunction with a conventional cracking catalyst, such as a large pore molecular sieve having a pore size greater than 7 Angstrom.

10 Claims, 1 Drawing Sheet

CATALYTIC CRACKING PROCESSING USING AN MCM-68 CATALYST

CROSS REFERENCE TO RELATED APPLICATIONS

Figure 1:
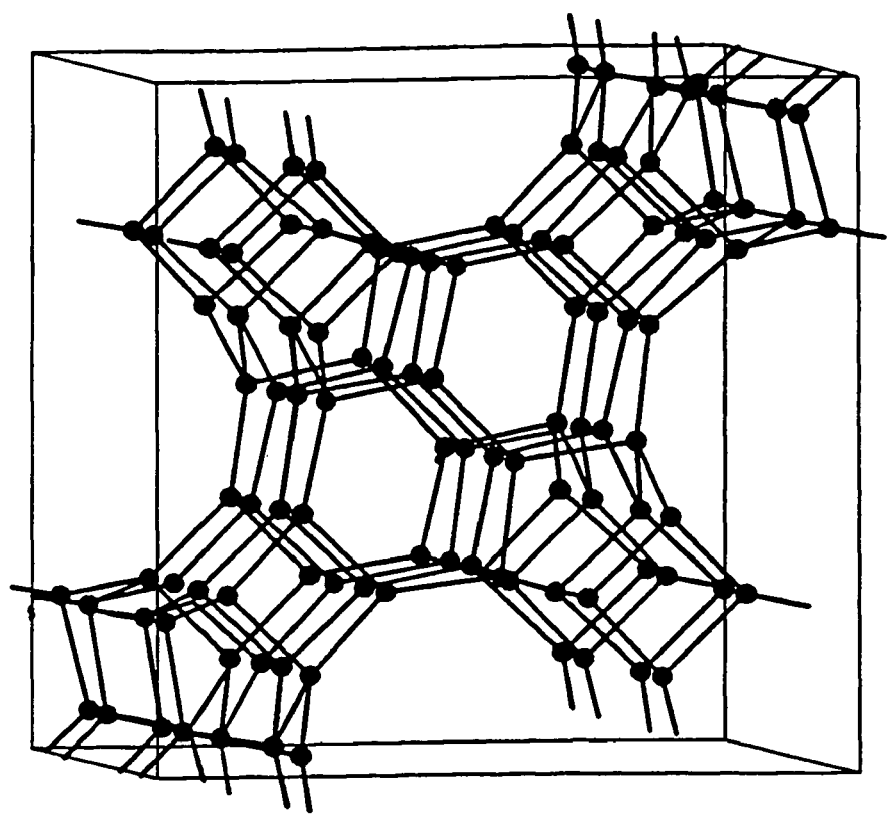

This application is a 371 of PCT/US00/01448 Jan. 21, 2000

This invention relates to a process for catalytic cracking of hydrocarbon feeds and, in particular to process for catalytic cracking of hydrocarbon feeds using a catalyst comprising MCM-68.

Catalytic cracking, and particularly fluid catalytic cracking (FCC), is routinely used to convert heavy hydrocarbon feedstocks to lighter products, such as gasoline and distillate range fractions. There is, however, an increasing need to enhance the yield of light olefins, especially $C_3$ to $C_5$ olefins, in the product slate from catalytic cracking processes. For example, $C_3$ to $C_5$ olefins are useful in making ethers and alkylate which are in high demand as octane enhancing additives for gasoline.

Conventional processes for catalytic cracking of heavy hydrocarbon feedstocks to gasoline and distillate fractions typically use a large pore molecular sieve, such as zeolite Y, as the primary cracking component. It is also well-known to add a medium pore zeolite, such as ZSM-5, to the cracking catalyst composition to increase the octane number of the gasoline fraction (see, for example, U.S. Pat. No. 4,828,679).

U.S. Pat. No. 5,472,594 discloses that the yield of $C_4$ and $C_5$ olefins in catalytic cracking can be enhanced by adding a phosphorus-containing medium pore zeolite, such as ZSM-5, to a conventional zeolite Y cracking catalyst such that the weight ratio of phosphorus-containing medium pore zeolite to zeolite Y is in the range 0.005 to 0.10.

It is also known from, for example, U.S. Pat. No. 4,740,292 that zeolite beta can be added to a conventional zeolite Y cracking catalyst so as increase the yield of $C_4$ olefins. However, the commercial utility of this process has to date been limited by the hydrothermal stability of existing forms of zeolite beta.

According to the present invention, it has now been found that the novel zeolite, MCM-68, has activity for catalytic cracking, both as the primary cracking catalyst and as an additive catalyst in conjunction with a conventional cracking catalyst. In particular, when used as an additive catalyst, MCM-68 exhibits improved selectivity toward butylenes and isobutane, as well improving the octane of the gasoline fraction. MCM-68 also exhibits excellent hydrothermal stability.

Thus the present invention resides in a process for catalytic cracking of a hydrocarbon feedstock comprising contacting the feedstock with a catalyst composition comprising a porous crystalline material, MCM-68, which contains at least one channel system, in which each channel is defined by a 12-membered ring of tetrahedrally coordinated atoms, and at least two further, independent channel systems, in each of which each channel is defined by a 10-membered ring of tetrahedrally coordinated atoms, wherein the number of unique 10-membered ring channels is twice the number of 12-membered ring channels.

Preferably, the porous crystalline material comprises with a framework of tetrahedral atoms bridged by oxygen atoms, the tetrahedral atom framework being defined by a unit cell with atomic coordinates in nanometers shown in Table 1, wherein each coordinate position may vary within ±0.05 nm.

Preferably, the catalyst composition also comprises a large pore molecular sieve having a pore size greater than about 7 Angstrom.

Figure 2:
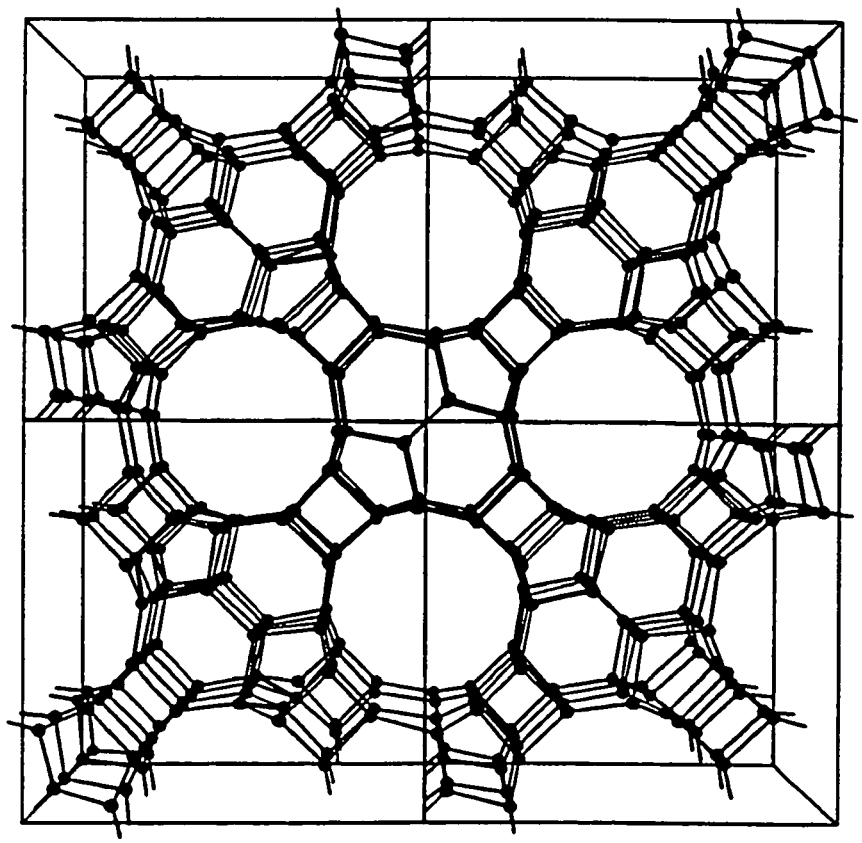

FIG. 1 is a schematic, three-dimensional illustration of a unit cell of MCM-68, showing only the tetrahedral atoms and the linkage between the tetrahedral atoms, and FIG. 2 is a schematic, three-dimensional illustration similar to FIG. 1 but of a plurality of unit cells.

The present invention provides a process for converting feedstock hydrocarbon compounds to product hydrocarbon compounds of lower molecular weight than the feedstock hydrocarbon compounds. In particular, the present invention provides a process for catalytically cracking a hydrocarbon feed to a mixture of products comprising gasoline, alkylate, and $C_3$–$C_5$ olefins and paraffins in the presence of a cracking catalyst under catalytic cracking conditions. Catalytic cracking units which are amenable to the process of the invention operate at temperatures from 200° to 870° C. and under reduced, atmospheric or superatmospheric pressure. The catalytic process can be either fixed bed, moving bed or fluidized bed and the hydrocarbon flow may be either concurrent or countercurrent to the catalyst flow. The process of the invention is particularly applicable to the Fluid Catalytic Cracking (FCC) or Thermofor Catalytic Cracking (TCC) processes.

The TCC process is a moving bed process and the catalyst is in the shape of pellets or beads having an average particle size of about one-sixty-fourth to one-fourth inch. Active, hot catalyst beads progress downwardly concurrent with a hydrocarbon charge stock through a cracking reaction zone. The hydrocarbon products are separated from the coked catalyst and recovered, and the catalyst is recovered at the lower end of the zone and regenerated. Typically TCC conversion conditions include an average reactor temperature of from 450° to 510° C.; catalyst/oil volume ratio of from 2 to 7; reactor space velocity of 1 to 2.5 vol./hr./vol.; and recycle to fresh feed ratio of 0 to 0.5 (volume).

The process of the invention is particularly applicable to fluid catalytic cracking (FCC), in which the cracking catalyst is typically a fine powder with a particle size of 10 to 200 microns. This powder is generally suspended in the feed and propelled upward in a reaction zone. A relatively heavy hydrocarbon feedstock, e.g., a gas oil, is admixed with the cracking catalyst to provide a fluidized suspension and cracked in an elongated reactor, or riser, at elevated temperatures to provide a mixture of lighter hydrocarbon products. The gaseous reaction products and spent catalyst are discharged from the riser into a separator, e.g., a cyclone unit, located within the upper section of an enclosed stripping vessel, or stripper, with the reaction products being conveyed to a product recovery zone and the spent catalyst entering a dense catalyst bed within the lower section of the stripper. In order to remove entrained hydrocarbons from the spent catalyst prior to conveying the latter to a catalyst regenerator unit, an inert stripping gas, e.g., steam, is passed through the catalyst bed where it desorbs such hydrocarbons conveying them to the product recovery zone. The fluidizable catalyst is continuously circulated between the riser and the regenerator and serves to transfer heat from the latter to the former thereby supplying the thermal needs of the cracking reaction which is endothermic.

Typically, FCC conversion conditions include a riser top temperature of from 500° to 595° C., preferably from 520° to 565° C., and most preferably from 530° C. to 550° C.; catalyst/oil weight ratio of 3 to 12, preferably 4 to 11, and most preferably from 5 to 10; and catalyst residence time of 0.5 to 15 seconds, preferably from 1 to 10 seconds.

The hydrocarbon feedstock to be cracked may include, in whole or in part, a gas oil (e.g., light, medium, or heavy gas oil) having an initial boiling point above 204° C., a 50% point of at least 260° C. and an end point of at least 315° C. The feedstock may also include vacuum gas oils, thermal oils, residual oils, cycle stocks, whole top crudes, tar sand oils, shale oils, synthetic fuels, heavy hydrocarbon fractions derived from the destructive hydrogenation of coal, tar, pitches, asphalts, hydrotreated feedstocks derived from any of the foregoing, and the like. As will be recognized, the distillation of higher boiling petroleum fractions above 400° C. must be carried out under vacuum in order to avoid thermal cracking. The boiling temperatures utilized herein are expressed for convenience in terms of the boiling point corrected to atmospheric pressure. Resids or deeper cut gas oils with high metals contents can also be cracked using the process of the invention.

The catalyst composition used in the process of the invention comprises the novel porous crystalline material, MCM-68, either as the primary cracking component or as an additive component in conjunction with a conventional cracking catalyst. MCM-68 is a single phase crystalline material which has a unique 3-dimensional channel system comprising at least one channel system, in which each channel is defined by a 12-membered ring of tetrahedrally coordinated atoms, and at least two further independent channel systems, in which each channel is defined by a 10-membered ring of tetrahedrally coordinated atoms, wherein the number of unique 10-membered ring channels is twice the number of 12-membered ring channels. The normal crystalline form of MCM-68 contains one 12-membered ring channel system and two 10-membered ring channel systems, in which the channels of each system extend perpendicular to the channels of the other systems and in which the 12-ring channels are generally straight and the 10-ring channels are tortuous (sinusoidal).

The structure of MCM-68 may be defined by its unit cell, which is the smallest structural unit containing all the structural elements of the material. Table 1 lists the positions of each tetrahedral atom in the unit cell in nanometers; each tetrahedral atom is bonded to an oxygen atom which is also bonded to an adjacent tetrahedral atom. The structure represented by Table 1 is shown in FIG. 1 (which shows only the tetrahedral atoms). More extended versions of the structure are simply generated by attaching identical unit cells in any of the x, y or z directions. A more extended structure, illustrating the pores, is shown in FIG. 2. Since the tetrahedral atoms may move about due to other crystal forces (presence of inorganic or organic species, for example), a range of ±0.05 nm is implied for each coordinate position.

|   |    | x     | y     | z     |
|---|----|-------|-------|-------|
| T | 1  | 0.242 | 1.370 | 0.242 |
| T | 2  | 0.241 | 1.372 | 0.552 |
| T | 3  | 0.051 | 0.400 | 0.152 |
| T | 4  | 0.244 | 0.463 | 0.383 |
| T | 5  | 0.056 | 0.406 | 0.623 |
| T | 6  | 0.110 | 0.110 | 0.244 |
| T | 7  | 0.110 | 0.110 | 0.554 |
| T | 8  | 0.247 | 0.464 | 0.856 |
| T | 9  | 1.587 | 0.459 | 0.242 |
| T | 10 | 1.588 | 0.457 | 0.552 |
| T | 11 | 1.778 | 1.429 | 0.152 |
| T | 12 | 1.585 | 1.366 | 0.383 |
| T | 13 | 1.772 | 1.422 | 0.623 |
| T | 14 | 1.718 | 1.718 | 0.244 |

-continued

|   |    | x     | y     | z     |
|---|----|-------|-------|-------|
| T | 15 | 1.718 | 1.718 | 0.554 |
| T | 16 | 1.582 | 1.365 | 0.856 |
| T | 17 | 1.373 | 1.156 | 1.250 |
| T | 18 | 1.372 | 1.156 | 1.561 |
| T | 19 | 0.515 | 0.965 | 1.161 |
| T | 20 | 0.451 | 1.158 | 1.391 |
| T | 21 | 0.508 | 0.971 | 1.632 |
| T | 22 | 0.804 | 1.025 | 1.253 |
| T | 23 | 0.804 | 1.025 | 1.563 |
| T | 24 | 0.451 | 1.161 | 1.865 |
| T | 25 | 0.455 | 0.672 | 1.250 |
| T | 26 | 0.457 | 0.673 | 1.561 |
| T | 27 | 1.314 | 0.864 | 1.161 |
| T | 28 | 1.377 | 0.671 | 1.391 |
| T | 29 | 1.321 | 0.858 | 1.632 |
| T | 30 | 1.025 | 0.804 | 1.253 |
| T | 31 | 1.025 | 0.804 | 1.563 |
| T | 32 | 1.378 | 0.668 | 1.865 |
| T | 33 | 0.672 | 0.455 | 0.767 |
| T | 34 | 0.673 | 0.457 | 0.456 |
| T | 35 | 0.864 | 1.314 | 0.856 |
| T | 36 | 0.671 | 1.377 | 0.626 |
| T | 37 | 0.858 | 1.321 | 0.385 |
| T | 38 | 0.804 | 1.025 | 0.764 |
| T | 39 | 0.804 | 1.025 | 0.455 |
| T | 40 | 0.668 | 1.378 | 0.153 |
| T | 41 | 1.156 | 1.373 | 0.767 |
| T | 42 | 1.156 | 1.372 | 0.456 |
| T | 43 | 0.965 | 0.515 | 0.856 |
| T | 44 | 1.158 | 0.451 | 0.626 |
| T | 45 | 0.971 | 0.508 | 0.385 |
| T | 46 | 1.025 | 0.804 | 0.764 |
| T | 47 | 1.025 | 0.804 | 0.455 |
| T | 48 | 1.161 | 0.451 | 0.153 |
| T | 49 | 1.370 | 0.242 | 1.775 |
| T | 50 | 1.372 | 0.241 | 1.465 |
| T | 51 | 0.400 | 0.051 | 1.865 |
| T | 52 | 0.463 | 0.244 | 1.635 |
| T | 53 | 0.406 | 0.056 | 1.394 |
| T | 54 | 0.110 | 0.110 | 1.773 |
| T | 55 | 0.110 | 0.110 | 1.463 |
| T | 56 | 0.464 | 0.247 | 1.161 |
| T | 57 | 0.459 | 1.587 | 1.775 |
| T | 58 | 0.457 | 1.588 | 1.465 |
| T | 59 | 1.429 | 1.778 | 1.865 |
| T | 60 | 1.366 | 1.585 | 1.635 |
| T | 61 | 1.422 | 1.772 | 1.394 |
| T | 62 | 1.718 | 1.718 | 1.773 |
| T | 63 | 1.718 | 1.718 | 1.463 |
| T | 64 | 1.365 | 1.582 | 1.161 |
| T | 65 | 1.587 | 0.459 | 1.775 |
| T | 66 | 1.588 | 0.457 | 1.465 |
| T | 67 | 1.778 | 1.429 | 1.865 |
| T | 68 | 1.585 | 1.366 | 1.635 |
| T | 69 | 1.772 | 1.422 | 1.394 |
| T | 70 | 1.582 | 1.365 | 1.161 |
| T | 71 | 0.242 | 1.370 | 1.775 |
| T | 72 | 0.241 | 1.372 | 1.465 |
| T | 73 | 0.051 | 0.400 | 1.865 |
| T | 74 | 0.244 | 0.463 | 1.635 |
| T | 75 | 0.056 | 0.406 | 1.394 |
| T | 76 | 0.247 | 0.464 | 1.161 |
| T | 77 | 0.455 | 0.672 | 0.767 |
| T | 78 | 0.457 | 0.673 | 0.456 |
| T | 79 | 1.314 | 0.864 | 0.856 |
| T | 80 | 1.377 | 0.671 | 0.626 |
| T | 81 | 1.321 | 0.858 | 0.385 |
| T | 82 | 1.378 | 0.668 | 0.153 |
| T | 83 | 1.373 | 1.156 | 0.767 |
| T | 84 | 1.372 | 1.156 | 0.456 |
| T | 85 | 0.515 | 0.965 | 0.856 |
| T | 86 | 0.451 | 1.158 | 0.626 |
| T | 87 | 0.508 | 0.971 | 0.385 |
| T | 88 | 0.451 | 1.161 | 0.153 |
| T | 89 | 1.156 | 1.373 | 1.250 |
| T | 90 | 1.156 | 1.372 | 1.561 |
| T | 91 | 0.965 | 0.515 | 1.161 |

-continued

| | | x | y | z |
|---|---|---|---|---|
| T | 92 | 1.158 | 0.451 | 1.391 |
| T | 93 | 0.971 | 0.508 | 1.632 |
| T | 94 | 1.161 | 0.451 | 1.865 |
| T | 95 | 0.672 | 0.455 | 1.250 |
| T | 96 | 0.673 | 0.457 | 1.561 |
| T | 97 | 0.864 | 1.314 | 1.161 |
| T | 98 | 0.671 | 1.377 | 1.391 |
| T | 99 | 0.858 | 1.321 | 1.632 |
| T | 100 | 0.668 | 1.378 | 1.865 |
| T | 101 | 0.459 | 1.587 | 0.242 |
| T | 102 | 0.457 | 1.588 | 0.552 |
| T | 103 | 1.429 | 1.778 | 0.152 |
| T | 104 | 1.366 | 1.585 | 0.383 |
| T | 105 | 1.422 | 1.772 | 0.623 |
| T | 106 | 1.365 | 1.582 | 0.856 |
| T | 107 | 1.370 | 0.242 | 0.242 |
| T | 108 | 1.372 | 0.241 | 0.552 |
| T | 109 | 0.400 | 0.051 | 0.152 |
| T | 110 | 0.463 | 0.244 | 0.383 |
| T | 111 | 0.406 | 0.056 | 0.623 |
| T | 112 | 0.464 | 0.247 | 0.856 |

MCM-68 can be prepared in essentially pure form with little or no detectable impurity crystal phases and, in its calcined form, has an X-ray diffraction pattern which is distinguished from the patterns of other known as-synthesized or thermally treated crystalline materials by the lines listed in Table 2. In its as-synthesized form, the crystalline MCM-68 material of the invention has an X-ray diffraction pattern which is distinguished from the patterns of other known as-synthesized or thermally treated crystalline materials by the lines listed in Table 3.

TABLE 2

| d(Å) | Relative Intensity [100 × I/I(o)] |
|---|---|
| 13.60 +/− 0.39 | S |
| 13.00 +/− 0.37 | VS |
| 10.92 +/− 0.31 | M |
| 10.10 +/− 0.29 | M |
| 9.18 +/− 0.26 | VS |
| 8.21 +/− 0.23 | W |
| 4.58 +/− 0.13 | W |
| 4.54 +/− 0.13 | W |
| 4.45 +/− 0.13 | VW–W |
| 4.32 +/− 0.12 | VW |
| 4.22 +/− 0.12 | VW |
| 4.10 +/− 0.12 | VS |
| 4.05 +/− 0.11 | M |
| 3.94 +/− 0.11 | M |
| 3.85 +/− 0.11 | M |
| 3.80 +/− 0.11 | VW |
| 3.40 +/− 0.10 | W |
| 3.24 +/− 0.09 | W |
| 2.90 +/− 0.08 | VW |

TABLE 3

| d(Å) | Relative Intensity [100 × I/I(o)] |
|---|---|
| 13.56 +/− 0.39 | VW |
| 12.93 +/− 0.37 | M–S |
| 10.92 +/− 0.31 | W |
| 10.16 +/− 0.29 | VW–W |
| 9.15 +/− 0.26 | VW–W |
| 8.19 +/− 0.23 | VW |
| 4.58 +/− 0.13 | W |
| 4.54 +/− 0.13 | W |
| 4.44 +/− 0.12 | W |
| 4.32 +/− 0.12 | VW |

TABLE 3-continued

| d(Å) | Relative Intensity [100 × I/I(o)] |
|---|---|
| 4.23 +/− 0.12 | VW |
| 4.10 +/− 0.12 | VS |
| 4.06 +/− 0.12 | M |
| 3.98 +/− 0.11 | W |
| 3.88 +/− 0.11 | M |
| 3.80 +/− 0.11 | VW |
| 3.40 +/− 0.10 | VW |
| 3.24 +/− 0.09 | W |
| 2.90 +/− 0.08 | VW |

These X-ray diffraction data were collected with a Scintag diffraction system, equipped with a germanium solid state detector, using copper K-alpha radiation. The diffraction data were recorded by step-scanning at 0.02 degrees of two-theta, where theta is the Bragg angle, and a counting time of 10 seconds for each step. The interplanar spacings, d's, were calculated in Angstrom units, and the relative intensities of the lines, $I/I_o$ is one-hundredth of the intensity of the strongest line, above background, were derived with the use of a profile fitting routine (or second derivative algorithm). The intensities are uncorrected for Lorentz and polarization effects. The relative intensities are given in terms of the symbols vs=very strong (80–100), s=strong (60–80), m=medium (40–60), w=weak (20–40), and vw=very weak (0–20). It should be understood that diffraction data listed for this sample as single lines may consist of multiple overlapping lines which under certain conditions, such as differences in crystallographic changes, may appear as resolved or partially resolved lines. Typically, crystallographic changes can include minor changes in unit cell parameters and/or a change in crystal symmetry, without a change in the structure. These minor effects, including changes in relative intensities, can also occur as a result of differences in cation content, framework composition, nature and degree of pore filling, crystal size and shape, preferred orientation and thermal and/or hydrothermal history.

MCM-68 has a composition involving the molar relationship:

$$X_2O_3:(n)YO_2,$$

wherein X is a trivalent element, such as aluminum, boron, iron, indium, and/or gallium, preferably aluminum; Y is a tetravalent element such as silicon, tin, titanium and/or germanium, preferably silicon; and n is at least 5, such as 5 to 100,000, and usually from 8 to 50. In the as-synthesized form, the material has a formula, on an anhydrous basis and in terms of moles of oxides per n moles of $YO_2$, as follows:

$$(0.1–2)M_2O:(0.2–2)Q:X_2O_3:(n)YO_2$$

wherein M is an alkali or alkaline earth metal, and Q is an organic moiety. The M and Q components are associated with the material as a result of their presence during crystallization, and are easily removed by post-crystallization methods hereinafter more particularly described.

MCM-68 can be prepared from a reaction mixture containing sources of alkali or alkaline earth metal (M), e.g., sodium and/or potassium, cation, an oxide of trivalent element X, e.g., aluminum and/or boron, an oxide of tetravalent element Y, e.g., silicon, directing agent (Q), and water, said reaction mixture having a composition, in terms of mole ratios of oxides, within the following ranges:

| Reactants | Useful | Preferred |
|---|---|---|
| YO$_2$/X$_2$O$_3$ | at least 5 | 8–50 |
| H$_2$O/YO$_2$ | 10–1000 | 15–100 |
| OH$^-$/YO$_2$ | 0.05–2 | 0.1–0.5 |
| M/YO$_2$ | 0.05–2 | 0.1–0.5 |
| Q/YO$_2$ | 0.01–1 | 0.05–0.2 |

The organic directing agent Q used herein is selected from the novel dications N,N,N',N'-tetraalkylbicyclo[2.2.2]oct-7-ene-2,3:5,6-dipyrrolidinium dication and N,N,N',N'-tetraalkylbicyclo[2.2.2]octane-2,3:5,6-dipyrrolidinium dication which can be represented by the following formulae:

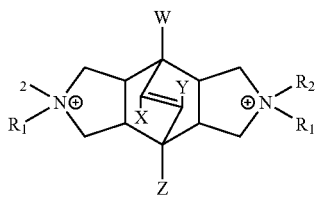

N,N,N',N'-tetraalkylbicyclo[2.2.2]oct-7-ene-2,3:5,6-dipyrrolidinium

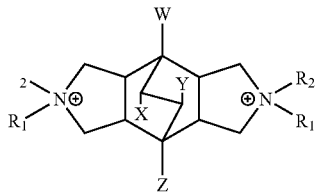

N,N,N',N'-tetraalkylbicyclo[2.2.2]octane-2,3:5,6-dipyrrolidinium where $R_1$, $R_2$ may be the same or different substituents selected from alkyl groups having 1 to 6 carbon atoms, phenyl and benzyl groups, or $R_1$ and $R_2$ may be linked as a cyclic group having 3 to 6 carbon atoms; and W, X, Y, Z may be the same or different substituents selected from hydrogen, alkyl groups having 1 to 6 carbon atoms, phenyl groups and halogens. In a preferred example, the organic directing agent is the N,N,N',N'-tetraethyl-exo,exo-bicyclo[2.2.2]oct-7-ene-2,3:5,6-dipyrrolidinium (Bicyclodiquat-Et$_4$) dication, having the formula $C_{20}H_{36}N_2^{++}$, which may be represented as follows:

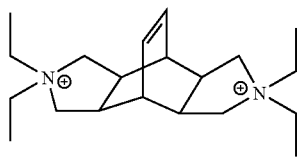

The source of the organic dication may be any salt which is not detrimental to the formation of the crystalline material of the invention, for example, the halide, e.g., iodide, or hydroxide salt.

The novel organic dications used to synthesize the MCM-68 of the invention can be prepared from, for example, exo,exo-bicyclo[2.2.2]oct-7-ene-2,3:5,6-tetracarboxylic dianhydride, which is a commercially available material. The dianhydride is initially reacted with ammonia or an amine to produce a diimide which is then reduced with LiAlH$_4$ to produce the diamine. The diamine can then be alkylated with an alkyl, phenyl or benzyl halide to produce the quaternary dication. Similarly, the bicyclooctane diquat can be produced from the dianhydride, which is known in the literature, or can be prepared by hydrogenation of the bicyclooctene dianhydride.

Crystallization of MCM-68 can be carried out at either static or stirred conditions in a suitable reactor vessel, such as for example, polypropylene jars or teflon lined or stainless steel autoclaves, at a temperature of 80° to 250° C. for a time sufficient for crystallization to occur at the temperature used, e.g., from 12 hours to 100 days. Thereafter, the crystals are separated from the liquid and recovered.

It should be realized that the reaction mixture components can be supplied by more than one source. The reaction mixture can be prepared either batchwise or continuously. Crystal size and crystallization time will vary with the nature of the reaction mixture employed and the crystallization conditions.

Synthesis of MCM-68 may be facilitated by the presence of at least 0.01%, preferably 0.10% and still more preferably 1%, seed crystals (based on total weight) of crystalline product.

Prior to its use in the process of the invention, the as-synthesized MCM-68 is subjected to treatment to remove part or all of any organic constituent. This is conveniently achieved by heating at a temperature of at least 370° C. for at least 1 minute and generally not longer than 20 hours. While subatmospheric pressure can be employed for the thermal treatment, atmospheric pressure is desired for reasons of convenience. The thermal treatment can be performed at a temperature up to 925° C. The thermally treated product may then be converted into its active, hydrogen form, typically by the conventional steps of repeated ammonium exchange followed by calcination.

In its hydrogen form MCM-68 typically exhibits a high acid activity, with an alpha value of 900–1000. Alpha value is an approximate indication of the catalytic cracking activity of the catalyst compared to a standard catalyst and it gives the relative rate constant (rate of normal hexane conversion per volume of catalyst per unit time). It is based on the activity of silica-alumina cracking catalyst taken as an Alpha of 1 (Rate Constant=0.016 sec-1). The Alpha Test is described in U.S. Pat. No. 3,354,078; in the *Journal of Catalysis*, 4, 527 (1965); 6, 278 (1966); and 61, 395 (1980). The experimental conditions of the test used herein include a constant temperature of 538° C. and a variable flow rate as described in detail in the *Journal of Catalysis*, 61, 395 (1980).

In the process of the invention, the MCM-68 may be used as the primary cracking catalyst, either alone or in conjunction with an additive component, such as ZSM-5 or zeolite beta. Alternatively, the MCM-68 may used as an additive component in conjunction with a conventional cracking catalyst, preferably a large pore molecular sieve having a pore size greater than 7 Angstrom. Typically, the weight ratio of the MCM-68 to the large pore molecular sieve is 0.005 to 0.50, preferably 0.01 to 0.25.

The primary cracking component may be any conventional large-pore molecular sieve having cracking activity including zeolite X (U.S. Pat. No. 2,882,442); REX; zeolite Y (U.S. Pat. No. 3,130,007); Ultrastable Y zeolite (USY) (U.S. Pat. No. 3,449,070); Rare Earth exchanged Y (REY)

(U.S. Pat. No. 4,415,438); Rare Earth exchanged USY (REUSY); Dealuminated Y (DeAl Y) (U.S. Pat. No. 3,442,792; U.S. Pat. No. 4,331,694); Ultrahydrophobic Y (UHPY) (U.S. Pat. No. 4,401,556); and/or dealuminated silicon-enriched zeolites, e.g., LZ-210 (U.S. Pat. No. 4,678,765). Preferred are higher silica forms of zeolite Y. Zeolite ZK-5 (U.S. Pat. No. 3,247,195); zeolite ZK-4 (U.S. Pat. No. 3,314,752); ZSM-20 (U.S. Pat. No. 3,972,983); zeolite Beta (U.S. Pat. No. 3,308,069) and zeolite L (U.S. Pat. Nos. 3,216,789; and 4,701,315). Naturally occurring zeolites such as faujasite, mordenite and the like may also be used. These materials may be subjected to conventional treatments, such as impregnation or ion exchange with rare earth elements to increase stability. The preferred large pore molecular sieve of those listed above is a zeolite Y, more preferably an REY, USY or REUSY.

Other suitable large-pore crystalline molecular sieves include pillared silicates and/or clays; aluminophosphates, e.g., ALPO4-5, ALPO4-8, VPI-5; silicoaluminophosphates, e.g., SAPO-5, SAPO-37, SAPO-31, SAPO-40; and other metal aluminophosphates. These are variously described in U.S. Pat. Nos. 4,310,440; 4,440,871; 4,554,143; 4,567,029; 4,666,875; 4,742,033; 4,880,611; 4,859,314; and 4,791,083.

The cracking catalyst will also normally contain one or more matrix or binder materials which are resistant to the temperatures and other conditions e.g., mechanical attrition, which occur during cracking. It is generally necessary that the catalysts be resistant to mechanical attrition, that is, the formation of fines which are small particles, e.g., less than 20 micron. The cycles of cracking and regeneration at high flow rates and temperatures, such as in an FCC process, have a tendency to break down the catalyst into fines, as compared with an average diameter of catalyst particles of 60 to 90 microns. In an FCC process, catalyst particles range from 10 to 200 microns, preferably from 20 to 120 microns. Excessive generation of catalyst fines increases the refiner's catalyst costs.

The matrix may fulfill both physical and catalytic functions. Matrix materials include active or inactive inorganic materials such as clays, and/or metal oxides such as alumina or silica, titania, zirconia, or magnesia. The metal oxide may be in the form of a sol or a gelatinous precipitate or gel.

Use of an active matrix material in conjunction with the molecular sieve component that is combined therewith, may enhance the conversion and/or selectivity of the overall catalyst composition in certain hydrocarbon conversion processes. Inactive materials may serve as diluents to control the amount of conversion in a given process so that products can be obtained economically and in an orderly fashion without employing other means for controlling the rate of reaction. These materials may be incorporated as naturally occurring clays to improve the attrition resistance of the catalyst under commercial operating conditions.

Naturally occurring clays which can be composited with the catalyst include the montmorillonite and kaolin families which include the subbentonites, and the kaolins commonly known as Dixie, McNamee, Georgia and Florida clays or others in which the main mineral constituent is halloysite, kaolinite, dickite, nacrite or anauxite. Such clays can be used in the raw state as originally mined or initially subjected to calcination, acid treatment or chemical modification.

In addition to the foregoing materials, catalysts can be composited with a porous matrix material such as silica-alumina, silica-magnesia, silica-zirconia, silica-thoria, silica-beryllia, silica-titania, as well as ternary materials such as silica-alumina-thoria, silica-alumina-zirconia, silica-alumina-magnesia, silica-magnesia-zirconia. The matrix can be in the form of a cogel. A mixture of these components can also be used.

In general, the relative proportions of finely divided, crystalline molecular sieve component and inorganic oxide matrix may vary widely, with the molecular sieve content ranging from 1 to 90% by weight, and more usually from 2 to 80 weight percent of the composite.

The invention will now be more particularly described with reference to the following Examples:

EXAMPLE 1

Synthesis of N,N'-Diethyl-exo,exo-bicyclo[2.2.2] oct-7-ene-2,3:5,6-tetracarboxylic diimide To a 2000-ml 3-necked round-bottomed flask equipped with a magnetic stirring bar, a reflux condenser and a thermometer were attached. The flask was then charged with 70 wt. % ethylamine in water (515.25 g, 8 moles) followed by exo,exo-bicyclo[2.2.2]oct-7-ene-2,3:5,6-tetracarboxylic dianhydride (99.28 g, 0.4 moles) in portions along with vigorous stirring. After two hours of stirring at room temperature, water (300 ml) was added. The mixture was then stirred at 70° C. for 48 hours and then at 100° C. for 18 hours to drive off the excess amine. The reaction was then cooled to room temperature and the remaining ethylamine quenched with concentrated HCl in a dropwise fashion. The solid was then filtered under suction, washed with water (400 ml) and dried in a vacuum dessicator over drierite to give 120.90 g (100%) of diimide as white crystals.

Melting Point: 265–266° C.

NMR: Solvent=CDCl$_3$ $^{13}$C ($\delta$/ppm): 12.846; 33.411; 33.776; 42.763; 130.685; 176.438.

$^1$H($\delta$/ppm): 1.07 (6H, t); 2.97 (4H, s); 3.47 (4H, q4); 3.78 (2H, br.s); 6.10 (2H, t).

Combustion Analysis for $C_{16}H_{18}N_2O_4$

|  | % C | % H | % N |
|---|---|---|---|
| Calculated | 63.56 | 6.00 | 9.27 |
| Found | 63.45 | 6.00 | 9.21 |

EXAMPLE 2

Synthesis of N,N'-Diethyl-exo,exo-bicyclo[2.2.2] oct-7-ene-2,3:5,6-dipyrrolidine All glassware in this procedure was dried in an oven at 150° C. for at least 12 hours. A 2000-ml, 3-necked round-bottomed flask equipped with a magnetic stirring bar, a thermometer and a graduated pressure equalized addition funnel sealed with a septum cap was comprehensively flushed with N$_2$. To this a soxhlet extractor with a thimble containing N,N'-diethyl-exo,exo-bicyclo[2.2.2]oct-7-ene-2, 3:5,6-tetracarboxylic diimide (33.26 g, 110 mmol) topped with a reflux condenser and an inline gas bubbler was attached. The system was then charged with lithium aluminum hydride powder (12.52 g, 330 mmol) and anhydrous THF (1650 ml) via the addition funnel. After 24 hours of reflux to fully extract and deliver the diimide, the reaction was cooled to 5° C. Then the reaction was quenched with water (12.5 ml), 15% NaOH solution (12.5 ml) and water (37.6 ml) keeping the temperature below 10° C. After warming to room temperature and suction filtration of the solids followed by washing with dichloromethane (660 ml), water (220 ml) was added to the combined filtrates which were then acidified using conc. HCl to pH=1–2. The organic layer was then separated, water (220 ml) added and the pH adjusted to 1–2 with concentrated HCl. This aqueous layer was separated and combined with the previous aqueous fraction, rendered basic with 50% NaOH solution to pH=11–12 and extracted with dichloromethane (5×275 ml). These combined organic fractions were dried over $Na_2SO_4$, filtered and evaporated in vacuum to give a yellow/orange oil which may solidify upon cooling (22.56 g, 83%). The oil was extracted with ether (2×150 mL), the fractions being filtered, combined, dried over $Na_2SO_4$, re-filtered & the solvent evaporated under vacuum to give a gold oil which solidifies upon cooling (20.15 g, 74%). $^1H$ and $^{13}C$ NMR analysis of the crude yellow solid showed no visible impurities and the diamine was used in this form in the subsequent diiodide preparation. However, an analytical sample of the diamine was obtained by vacuum distillation of the yellow solid (10 mTorr, 106–110° C.) to give a clear oil (52% efficiency) which crystallizes to a white solid on cooling.

Melting Point: 57–58° C.
NMR: Solvent=$CDCl_3$
$^{13}C$ ($\delta$/ppm): 13.837; 35.491; 44.210; 49.831; 58.423; 135.294.
$^1H$($\delta$/ppm): 1.05 (6H, t); 1.85 (4H, t); 2.37 (4H, q4); 2.49 (6H, br.d); 3.04(4H, t); 6.07 (2H, t).

Combustion Analysis for $C_{16}H_{26}N_2$

|  | % C | % H | % N |
|---|---|---|---|
| Calculated | 77.99 | 10.64 | 11.37 |
| Found | 77.82 | 10.59 | 11.31 |

EXAMPLE 3

Synthesis of N,N,N',N'-Tetraethyl-exo,exo-bicyclo[2.2.2]oct-7-ene-2,3:5,6-dipyrrolidinium diiodide (Bicyclodiquat-$Et_4$ 2I)

To a 1000-ml 3-necked round-bottomed flask equipped with a magnetic stirring bar, a reflux condenser, a thermometer and a pressure equalized addition funnel containing a solution of iodoethane (67.37 g, 432 mmol) in ethanol (216 ml) were attached. The flask was then charged with N,N'-diethyl-exo,exo-bicyclo[2.2.2]oct-7-ene-2,3:5,6-dipyrrolidine (35.48 g, 144 mmol) and ethanol (144 ml). After stirring until all the solids had dissolved the iodoethane solution was added slowly and the mixture refluxed overnight. After subsequent cooling to 10° C., the solids were suction filtered and washed with acetone (144 ml). The resultant off-white solid was then refluxed in acetone (500 ml) for 15 minutes, suction filtered and dried in a vacuum dessicator over drierite to give a tan solid, 70.78 g (88%).

Melting Point: >270° C. (decomposition)
NMR: Solvent=$D_2O$
$^{13}C$ ($\delta$/ppm): 10.115; 10.932; 35.721; 42.597; 55.604; 58.370; 67.030; 130.870.
$^1H$($\delta$/ppm): 1.28 (12H, t); 2.85 (8H, br.s); 2.92 (2H, br.s); 3.32 (8H, q6); 3.81 (4H, d); 6.45 (2H, t).

Combustion Analysis for $C_{20}H_{36}N_2I_2$

|  | % C | % H | % N |
|---|---|---|---|
| Calculated | 43.02 | 6.50 | 5.02 |
| Found | 43.19 | 6.58 | 4.85 |

EXAMPLE 4

Synthesis of Aluminosilicate MCM-68

14 g of Colloidal Silica Sol (30 wt % of $SiO_2$: Aldrich Ludox SM-30), and 22.096 g of distilled water are mixed with 0.6056 g of $Al(OH)_3$ (Aluminum Hydroxide, solid). To this reaction mixture added 7.354 g of KOH (88.8% purity) (Potassium Hydroxide, 20 wt % solution) and then added 3.912 g of Bicyclodiqaut-$Et_4$ 2I$^-$ (N,N,N',N'-Tetraethyl-exo,exo-bicyclo[2.2.2]oct-7-ene-2,3:5,6-dipyrrolidinium diiodide, solid). The reaction can be represented by the following mole ratios:

| | |
|---|---|
| $Si/Al_2$ | 18 |
| $H_2O/Si$ | 30 |
| OH/Si | 0.375 |
| $K^+$/Si | 0.375 |
| Bicyclodiquat-$Et_4$ 2I/Si | 0.10 |

The combined mixture was added to an autoclave and heated to 160° C. for 300 hours unstirred. The product was then filtered and washed with water and dried overnight under an IR lamp. The solid is subsequently calcined in air at a temperature of 540° C. for 8 hours to yield the material designated as MCM-68.

EXAMPLE 5

Ammonium Exchange and Preparation of H-MCM-68

The calcined MCM-68 material from Example 4 was ion exchanged 4 four times with a 1M ammonium nitrate solution at 80° C. then filtered washed and dried under an IR lamp. Subsequently it was calcined at 540° C. in air for 8 hrs. The H-MCM-68 obtained had an alpha value of a 1000.

EXAMPLE 6

Synthesis of Aluminosilicate MCM-68

7 g of Colloidal Silica (30 wt %), $Al(OH)_3$ (Aluminum Hydroxide, solid), KOH (Potassium Hydroxide, 20 wt % solution), Bicyclodiqaut-$Et_4$ 2I (N,N,N',N'-Tetraethyl-exo,exo-bicyclo[2.2.2]oct-7-ene-2,3:5,6-dipyrrolidinium diiodide, solid) and distilled water were combined in the following mole ratios:

| | |
|---|---|
| $Si/Al_2$ | 30 |
| $H_2O/Si$ | 30 |
| OH/Si | 0.375 |
| $K^+$/Si | 0.375 |
| Bicyclodiquat-$Et_4$ 2I/Si | 0.10 |

The combined mixture was added to an autoclave and heated to 160° C. for 150 hours. The product was then filtered and washed with water and dried overnight under an IR lamp. The solid was subsequently calcined in air at a temperature of 540° C. for 8 hours to yield the MCM-68. The powder x-ray diffraction of the final product showed the presence of trace amounts of zeolite ZSM-12.

EXAMPLE 7

Synthesis of Aluminosilicate MCM-68

7 g of Colloidal Silica (30 wt. %), Al(OH)$_3$ (Aluminum Hydroxide, solid), KOH (Potassium Hydroxide, 20 wt. % solution), Bicyclodiqaut-Et$_4$ 2I (N,N,N',N'-Tetraethyl-exo, exo-bicyclo[2.2.2]oct-7-ene-2,3:5,6-dipyrrolidinium diiodide, solid) and distilled water were combined in the following mole ratios:

| | |
|---|---|
| Si/Al$_2$ | 15 |
| H$_2$O/Si | 30 |
| OH/Si | 0.375 |
| K$^+$/Si | 0.375 |
| Bicyclodiquat-Et$_4$ 2I/Si | 0.10 |

The combined mixture was added to an autoclave and heated to 160° C. for 240 hours. The product was then filtered and washed with water and dried overnight under an IR lamp. The solid was subsequently calcined in air at a temperature of 540° C. for 8 hours to yield MCM-68. The powder x-ray diffraction of the final product indicated the presence of trace amounts of zeolite Beta.

EXAMPLE 8

Synthesis of Aluminosilicate MCM-68

14 g of Colloidal Silica (30 wt. %), Al(OH)$_3$ (Aluminum Hydroxide, solid), KOH (Potassium Hydroxide, 20 wt. % solution), Bicyclodiqaut-Et$_4$ 2I (N,N,N',N'-Tetraethyl-exo, exo-bicyclo[2.2.2]oct-7-ene-2,3:5,6-dipyrrolidinium diiodide, solid) and distilled water were combined in the following mole ratios:

| | |
|---|---|
| Si/Al$_2$ | 18 |
| H$_2$O/Si | 30 |
| OH/Si | 0.375 |
| K$^+$/Si | 0.375 |
| Bicyclodiquat-Et$_4$ 2I/Si | 0.10 |

The combined mixture was added to an autoclave and heated to 170° C. for 200 hours at 200 rpm. The product was then filtered and washed with water and dried overnight under an IR lamp. The solid was subsequently calcined in air at a temperature of 540° C. for 8 hours to yield MCM-68.

EXAMPLE 9

Synthesis of Aluminosilicate MCM-68 with 2 wt. % Seeds of as-Synthesized MCM-68

7 g of Colloidal Silica (30 wt. %), Al(OH)$_3$ (Aluminum Hydroxide, solid), KOH (Potassium Hydroxide, 20 wt. % solution), Bicyclodiqaut-Et$_4$ 2I (N,N,N',N'-Tetraethyl-exo, exo-bicyclo[2.2.2]oct-7-ene-2,3:5,6-dipyrrolidinium diiodide, solid) and distilled water were combined in the following mole ratios:

| | |
|---|---|
| Si/Al$_2$ | 18 |
| H$_2$O/Si | 30 |
| OH/Si | 0.375 |
| K$^+$/Si | 0.375 |
| Bicyclodiquat-Et$_4$ 2I/Si | 0.10 |

To this mixture were added 2 wt. % seed crystals of as-synthesized MCM-68 from Example 5. The combined mixture was added to an autoclave and heated to 160° C. for 200 hours. The product was then filtered and washed with water and dried overnight under an IR lamp. The solid was subsequently calcined in air at a temperature of 540° C. for 8 hours to yield the material designated as MCM-68.

EXAMPLE 10

Hydrothermal Stability of MCM-68

The hydrothermal stability of the calcined H-MCM-68 of Example 5 was evaluated by steaming the crystals in a tube steamer at 1500° F. (815° C.) for 4 hour, and then the retention of the surface area was measured. As shown in Table 4, MCM-68 exhibits excellent hydrothermal stability in that 77% of the initial surface area was maintained after the severe steaming.

TABLE 4

| | MCM-68 |
|---|---|
| Calcined-Only | |
| Surface Area, m$^2$/g | 547 |
| Alpha | 730 |
| Steaming at 1500° F. for 4 Hours | |
| Surface Area, m$^2$/g | 421 |
| % Retention of Surface area | 77% |

EXAMPLE 11

Preparation of a MCM-68/Silica-Clay Catalyst

A blend containing 40 wt. % H-form MCM-68 crystals from Example 5, 30 wt. % aqueous colloidal silica, and 30 wt. % Kaolin clay was prepared (on 100% ash basis). While grinding the mixture lightly, a small amount of water was added to form a homogeneous paste. The paste was air dried to form a hard cake. Then the dry cake was sized with a mortar and pastel, and fine particles separated in between 40 and 105 micron filters were collected. Then the 40–105 micron fluidizable MCM-68 catalyst was calcined in air at 1000° F. (540° C.) for 3 hours.

EXAMPLE 12

Preparation of a Beta/Silica-Clay Catalyst

A zeolite beta catalyst was prepared following a procedure similar to Example 11 except H-form Zeolite Beta with a 35/1 SiO$_2$Al$_2$O$_3$ was used instead of MCM-68.

EXAMPLE 13

Preparation of a USY/Silica-Clay Catalyst

A USY catalyst was prepared using the procedure of Example 11 except H-form USY with a 5.4 $SiO_2/Al_2O_3$ and 24.54 Å Unit Cell Size was used instead of MCM-68.

EXAMPLE 14

Performance as FCC Additive Catalysts After Severe Steaming

Before evaluation in a pilot unit, the catalysts (Examples 11 through 13) were deactivated at 1500° F. (815° C.) for 4 hours at 100% steam to simulate deactivation in a FCC regenerator. The USY/Silica-Clay catalyst (Example 13) after steam deactivation was evaluated alone for a base case. The MCM-68 and beta catalysts (Examples 11 and 12) were each evaluated as an additive catalyst in conjunction with the USY/Silica-Clay catalyst. Twenty-five (25) weight percent of an additive catalyst after steam deactivation was blended with 75 wt. % of steam deactivated USY catalyst.

A Light Vacuum Gas Oil feed having the properties shown in Table 5 was used to evaluate the catalysts.

TABLE 5

| Charge Stock Properties | Vacuum Gas Oil (VGO) |
| --- | --- |
| API Gravity @ 60° F. | 23.2 |
| Aniline Point, ° F. | 139 |
| CCR, wt. % | 0.04 |
| Hydrogen, wt. % | 12.01 |
| Sulfur, wt. % | 2.2 |
| Total Nitrogen, ppm | 480 |
| Basic Nitrogen, ppm | 169 |
| Bromine Number | 7.8 |
| Distillation, ° F. for wt. % (SimDis) | |
| IBP, ° F. | 384 |
| 50 wt. %, ° F. | 671 |
| EP, ° F. | 960 |

A micro-gram-scale cracking unit made of a fixed bed catalyst reactor within a pyrolysis heater (Pyrojector II from SGE) was used in the evaluation. The pyrolysis-cracking unit was attached to a prep-scale GC and the cracked product was sent directly to the GC. The unit could not measure the coke and $H_2$ yields and hence the product, excluding $H_2$ and coke, was normalized to 100% for yield and conversion calculations. This method of data analysis was adequate to compare the incremental yields associated with an additive catalyst since the coke and $H_2$ yield differences among catalyst blends would be small. The GC peaks for propylene ($C_3^=$) and n-propane (n-$C_3$) were overlapped and could not be separated, thus only the combined $C_3$ yield was reported.

Reaction conditions used were 975° F. (524° C.) temperature and approximately 1–2 seconds of vapor contact time. A range of conversions was examined by varying the catalyst-to-oil ratios. Performances of the catalysts are summarized in Table 6, where the product data were interpolated to a constant conversion, 70 wt. % conversion of feed to 425° F. or less (425° F.$^-$) material. Gasoline yield was estimated for 125° to 425° F. range hydrocarbon product, and light fuel oil (LFO) for 425° to 660° F. For blend catalysts, yield shifts over the USY base case are reported.

TABLE 6

| Catalyst | USY | Beta/USY Blend | MCM68/USY Blend |
| --- | --- | --- | --- |
| Conversion, wt. % | 70 | 70 | 70 |
| Cat/Oil | 6.6 | 7 | 7.3 |
| | | Incremental Yields | |
| Total $C_1 + C_2$, wt. % | 0.8 | 0.0 | 0.0 |
| $C_2^=$, wt. % | 0.4 | 0.0 | −0.1 |
| Total $C_3$, wt. % | 6.5 | 0.8 | 0.5 |
| Total $C_4$, wt. % | 13.3 | 1.4 | 1.3 |
| $C_4^=$, wt. % | 10.3 | 1.1 | 1.3 |
| i-$C_4$, wt. % | 2.5 | 0.2 | 0.0 |
| $C_5^+$ Gasoline, wt. % | 49.5 | −2.3 | −1.9 |
| LFO, wt. % | 18.8 | −0.1 | 0.4 |
| HFO, wt. % | 11.1 | 0.2 | −0.2 |
| $\Delta C_4^=/\Delta$ Total $C_4$, wt/wt | Base | 0.79 | 1.00 |
| $\Delta(C_4^= + iC_4)/\Delta$ Total $C_4$, wt/wt | Base | 0.93 | 1.00 |
| $\Delta(C_4^= + iC_4)/\Delta$ Gasoline-loss, wt/wt | Base | 0.57 | 0.68 |
| $\Delta(C_4^= + iC_4 + $ Total $C_3)/\Delta$ Gasoline-loss, wt/wt | Base | 0.91 | 0.95 |

The results in Table 6 indicate that the MCM-68 additive catalyst produces additional $C_3$ and $C_4$ olefins, Gasoline-loss is a direct indication of the catalyst activity since the additive catalyst converts mainly the heavy gasoline range hydrocarbon molecules to light gasoline, and $C_3$–$C_4$ paraffins and olefins. The loss in gasoline yield will be more than offset by the alkylates produced with the $C_3$ and $C_4$ olefins. Compared to the zeolite Beta additive catalyst, MCM-68 catalyst make less $C_3$, and more $C_4^=$, suggesting that MCM-68 is even more $C_4$ olefin selective than Beta. MCM-68 exhibited slightly lower gasoline volume-loss than Beta, but produced more $C_4$ olefins. MCM-68 exhibited lower H-transfer activity and the incremental $C_4$ stayed as $C_4$ olefins.

EXAMPLE 15

Performance as FCC Additive Catalysts after Intermediate Steaming

MCM-68 was also compared with zeolite beta after milder steam deactivation conditions, e.g., at 1300° F. (700° C.) steaming to simulate intermediate catalyst deactivation in an FCC regenerator. Twenty-five (25) wt. % of an additive catalyst (Examples 11 and 12) after steam deactivation at 1300° F. for 4 hours was blended with 75 wt. % of steam deactivated USY catalyst. A USY/Silica-Clay catalyst (Example 13) after 1500' (815° C.) steam deactivation was evaluated alone for a base case. Performances of the catalysts are summarized in Table 7, where the product data were interpolated to a constant conversion, 74 wt. % conversion of feed to 425° F. or less (425° F.$^-$) material.

TABLE 7

| Catalyst | USY | Beta/USY Blend | MCM68/USY Blend |
| --- | --- | --- | --- |
| Conversion, wt. % | 74 | 74 | 74 |
| Cat/Oil | 10 | 5.9 | 5.7 |
| | | Incremental Yields | |
| Total $C_1 + C_2$, wt. % | 0.9 | 0.4 | 0.4 |
| $C_2^=$, wt. % | 0.5 | 0.2 | 0.3 |
| Total $C_3$, wt. % | 7.7 | 4.6 | 4.4 |
| Total $C_4$, wt. % | 14.5 | 4.5 | 4.4 |
| $C_4^=$, wt. % | 10.7 | 2.4 | 2.0 |

TABLE 7-continued

| Catalyst | USY | Beta/ USY Blend | MCM68/ USY Blend |
|---|---|---|---|
| i-$C_4$, wt. % | 3.3 | 2.1 | 2.3 |
| $C_5^+$ Gasoline, wt. % | 50.4 | −9.6 | −9.2 |
| LFO, wt. % | 17.0 | −1.0 | −1.4 |
| HFO, wt. % | 9.0 | 0.9 | 1.1 |
| $\Delta C_4^=/\Delta$ Total $C_4$, wt/wt | Base | 0.53 | 0.45 |
| $\Delta(C_4^= + IC_4)/\Delta$ Total $C_4$, wt/wt | Base | 1.00 | 0.98 |
| $\Delta(C_4^= + iC_4)/\Delta$ Gasoline-loss, wt/wt | Base | 0.47 | 0.47 |
| $\Delta(C_4^= + iC_4 +$ Total $C_3)/\Delta$ Gasoline-loss, wt/wt | Base | 0.95 | 0.95 |

The results summarized in Table 7 indicate that the MCM-68 additive catalyst cracks gasoline and LCO, and converts them to mainly $C_3$, $C_4$ olefins, and isobutane. The zeolite beta additive catalyst and the MCM-68 additive catalyst exhibit comparable $C_3$, $C_4^=$, and $iC_4$ yields.

EXAMPLE 16

Performance of MCM-68 Catalyst as FCC Base-Cracking Catalyst

MCM-68 catalyst (Example 11) after steam deactivation at 1500° F. (815° C.) for 4 hours at 100% steam was evaluated by itself with the Vacuum Gas Oil feed in Table 4. Performance of the MCM-68 for VGO cracking was compared with that of USY/Silica-Clay catalyst (Example 13) after steam deactivation at 1500° F. (815° C.) for 4 hours at 100% steam. Performance results are summarized in Table 8.

TABLE 8

| Catalyst | USY | MCM-68 |
|---|---|---|
| Conversion, wt. % | 52.9 | 37.7 |
| Cat/Oil | 4 | 8 |
| Total $C_1 + C_2$, wt. % | 0.4 | 0.4 |
| $C_2^=$, wt. % | 0.2 | 0.2 |
| Total $C_3$, wt. % | 3.0 | 4.8 |
| Total $C_4$, wt. % | 6.9 | 9.5 |
| $C_4^=$, wt. % | 5.5 | 8.9 |
| i-$C_4$, wt. % | 1.2 | 0.4 |
| $C_5^+$ Gasoline, wt. % | 42.6 | 23.0 |
| LEO, wt. % | 26.6 | 26.3 |
| HFO, wt. % | 20.4 | 36.0 |
| Wt. %(Total $C_3$ + Total $C_4$)/wt. % Converted, wt/wt | 19% | 38% |
| Wt. % $C_4^=$/wt. % converted, wt/wt | 10% | 24% |

The results summarized in Table 8 indicate that the MCM-68 catalyst cracks VGO effectively. Compared to USY, MCM-68 had lower cracking activity, but MCM-68 is far more selective in generating $C_3$, $C_4$ olefins, and isobutane. USY is a gasoline-selective catalyst where only 19% of the converted material became $C_3$ and $C_4$. MCM-68 is extremely olefin-selective in that 38% of the converted material became $C_3$ and $C_4$. Also MCM-68 catalyst shows excellent selectivity toward $C_4$ olefins.

The invention claimed is:

1. A process for catalytic cracking of a hydrocarbon feedstock comprising contacting the feedstock with a catalyst composition comprising a porous crystalline material which contains at least one channel system, in which each channel is defined by a 12-membered ring of tetrahedrally coordinated atoms, and at least two further, independent channel systems, in each of which each channel is defined by a 10-membered ring of tetrahedrally coordinated atoms, wherein the number of unique 10-membered ring channels is twice the number of 12-membered ring channels.

2. The process of claim 1 wherein said porous crystalline material contains one 12-membered ring channel system and two 10-membered ring channel systems.

3. The process of claim 2 in which the channels in each 10-membered ring channel system of crystalline material extend in a direction generally perpendicular to the channels in the other 10-membered ring channel system and to the channels in the 12-membered ring channel system.

4. A process for catalytic cracking of a hydrocarbon feedstock comprising contacting the feedstock with a catalyst composition comprising a synthetic porous crystalline material comprising a framework of tetrahedral atoms bridged by oxygen atoms, the tetrahedral atom framework being defined by a unit cell with atomic coordinates in nanometers shown in Table 1, wherein each coordinate position may vary within ±0.05 nanometer.

5. A process for catalytic cracking of a hydrocarbon feedstock comprising contacting the feedstock with a catalyst composition comprising a synthetic porous crystalline material characterized by an X-ray diffraction pattern including values substantially as set forth in Table 2 of the specification and having a composition comprising the molar relationship $$X_2O_3:(n)YO_2,$$

wherein n is at least 5, X is a trivalent element, and Y is a tetravalent element.

6. The process of claim 5 wherein X is a trivalent element selected from the group consisting of boron, iron, indium, gallium, aluminum, and a combination thereof; and Y is a tetravalent element selected from the group consisting of silicon, tin, titanium, germanium, and a combination thereof.

7. The process of claim 5 wherein X comprises aluminum and Y comprises silicon.

8. The process of claim 5, wherein the catalyst composition also comprises a large pore molecular sieve having a pore size greater than 7 Angstrom.

9. The process of claim 8, wherein the large pore molecular sieve is zeolite Y.

10. The process of claim 8, wherein the weight ratio of said synthetic porous crystalline material to the large pore molecular sieve is from 0.005 to 0.50.

* * * * *